US011085039B2

(12) United States Patent
Cochran et al.

(10) Patent No.: US 11,085,039 B2
(45) Date of Patent: *Aug. 10, 2021

(54) METHODS AND SYSTEMS FOR SCREENING USING MICROCAPILLARY ARRAYS

(71) Applicant: xCella Biosciences, Inc., Menlo Park, CA (US)

(72) Inventors: Jennifer R. Cochran, Stanford, CA (US); Bob Chen, East Palo Alto, CA (US); Spencer Caleb Alford, Mountain View, CA (US)

(73) Assignee: xCella Biosciences, Inc., San Diego, CA (US)

( * ) Notice: Subject to any disclaimer, the term of this patent is extended or adjusted under 35 U.S.C. 154(b) by 1188 days.

This patent is subject to a terminal disclaimer.

(21) Appl. No.: 15/376,588

(22) Filed: Dec. 12, 2016

(65) Prior Publication Data

US 2018/0163198 A1    Jun. 14, 2018

(51) Int. Cl.
| | | |
|---|---|---|
| C12N 15/10 | (2006.01) | |
| G01N 33/68 | (2006.01) | |
| B01L 3/00 | (2006.01) | |
| C12N 15/81 | (2006.01) | |
| G01N 33/53 | (2006.01) | |

(52) U.S. Cl.
CPC ...... *C12N 15/1055* (2013.01); *B01L 3/50857* (2013.01); *C12N 15/1037* (2013.01); *C12N 15/1086* (2013.01); *C12N 15/81* (2013.01); *G01N 33/53* (2013.01); *G01N 33/5308* (2013.01); *G01N 33/6845* (2013.01); *G01N 2500/10* (2013.01); *G01N 2500/20* (2013.01)

(58) Field of Classification Search
None
See application file for complete search history.

(56) References Cited

U.S. PATENT DOCUMENTS

| | | | |
|---|---|---|---|
| 4,111,754 A | 9/1978 | Park | |
| 4,621,059 A | 11/1986 | Rokugawa | |
| 4,960,566 A | 10/1990 | Mochida et al. | |
| 5,262,129 A | 11/1993 | Terada et al. | |
| 5,675,155 A | 10/1997 | Pentoney et al. | |
| 5,730,187 A | 3/1998 | Howitz et al. | |
| 5,763,263 A | 6/1998 | Dehlinger et al. | |
| 5,843,767 A | 12/1998 | Beattie et al. | |
| 6,027,873 A | 2/2000 | Schellenberger et al. | |
| 6,174,673 B1 | 1/2001 | Short et al. | |
| 6,306,578 B1 | 10/2001 | Schellenberger et al. | |
| 6,377,721 B1 | 4/2002 | Walt et al. | |
| 6,387,331 B1 | 5/2002 | Hunter et al. | |
| 6,436,632 B2 | 8/2002 | Liu et al. | |
| 6,547,941 B2 | 4/2003 | Kopf-Sill et al. | |
| 6,716,629 B2 | 4/2004 | Hess et al. | |
| 6,743,633 B1 | 6/2004 | Hunter et al. | |
| 6,794,127 B1 | 9/2004 | Lafferty et al. | |
| 6,816,257 B2 | 11/2004 | Goix et al. | |
| 6,823,079 B1 | 11/2004 | Winterot et al. | |
| 6,838,680 B2 | 1/2005 | Maher et al. | |
| 6,866,824 B2 | 3/2005 | Lafferty et al. | |
| 6,881,312 B2 | 4/2005 | Kopf-Sill et al. | |
| 6,893,877 B2 | 5/2005 | Hunter et al. | |
| 6,907,798 B2 | 6/2005 | Ganser et al. | |
| 6,972,183 B1 | 12/2005 | Lafferty et al. | |
| 6,977,723 B2 | 12/2005 | Lemmo et al. | |
| 7,012,676 B2 | 3/2006 | Baer et al. | |
| 7,019,827 B2 | 3/2006 | Lafferty et al. | |
| 7,221,455 B2 | 5/2007 | Chediak et al. | |
| 7,282,329 B2 | 10/2007 | Manalis et al. | |
| 7,403,280 B2 | 7/2008 | Beigel et al. | |
| 7,452,507 B2 | 11/2008 | Renzi et al. | |
| 7,547,556 B2 | 6/2009 | Hunter et al. | |
| 7,666,360 B2 | 2/2010 | Schellenberger et al. | |
| 7,666,630 B2 | 2/2010 | Yaver et al. | |

(Continued)

FOREIGN PATENT DOCUMENTS

| | | |
|---|---|---|
| AU | 6027873 | 3/1975 |
| AU | 6174673 | 4/1975 |

(Continued)

OTHER PUBLICATIONS

Chen et al (Nature Chemical Biology 12:76-81; public availability date Dec. 7, 2015) (Year: 2016).*
LEICA LMD6500, LEICA LMD7000 Laser Microdissection Systems brochure (2013).
Chen, Bob "High-Throughput Analysis and Protein Engineering Using Microcapillary Arrays. A Dissertation Submitted to the Department of Bioengineering and the Committee on Graduate Studies of Stanford University." (Jan. 2015).
Vandewoestyne, M. et al., "Laser capture microdissection: Should an ultraviolet or infrared laser be used?" Analytical Biochemistry, 439: 88-98 (2013).
Emmert-Buck, M. et al., "Laser Capture Microdissection." Science, vol. 274, pp. 998-1001 (1996).
Dobes, N. et al., "Laser-Based Directed Release of Array Elements for Efficient Collection into Targeted Microwells." Analyst., 138(3): 831-838 (2013).

(Continued)

*Primary Examiner* — Christopher M Gross
(74) *Attorney, Agent, or Firm* — Knobbe Martens Olson & Bear LLP

(57) ABSTRACT

High-throughput methods for screening large populations of variant proteins are provided. The methods utilize large-scale arrays of microcapillaries, where each microcapillary comprises a solution containing a variant protein, an immobilized target molecule, and a reporter element. Immobilized target molecules may include any molecule of interest, including proteins, nucleic acids, carbohydrates, and other biomolecules. The association of a variant protein with a molecular target is assessed by measuring a signal from the reporter element. The contents of microcapillaries identified in the assays as containing variant proteins of interest can be isolated, and cells expressing the variant proteins of interest can be characterized. Also provided are systems for performing the disclosed screening methods.

28 Claims, 11 Drawing Sheets

(56) References Cited

U.S. PATENT DOCUMENTS

| | | |
|---|---|---|
| 7,738,945 B2 | 6/2010 | Fauver et al. |
| 7,807,108 B2 | 10/2010 | Fasulka |
| 7,907,259 B2 | 3/2011 | Sagmuller et al. |
| 7,933,004 B2 | 4/2011 | Sugita et al. |
| 8,029,745 B2 | 10/2011 | Hunter et al. |
| 8,278,071 B2 | 10/2012 | Brown et al. |
| 8,325,342 B2 | 12/2012 | Ali et al. |
| 8,338,092 B2 | 12/2012 | Hofmann et al. |
| 8,460,878 B2 | 6/2013 | Walt et al. |
| 8,460,879 B2 | 6/2013 | Walt et al. |
| 8,492,098 B2 | 7/2013 | Walt et al. |
| 8,535,876 B2 | 9/2013 | Wesner et al. |
| 8,551,698 B2 | 10/2013 | Brown et al. |
| 8,623,596 B2 | 1/2014 | Gandini et al. |
| 8,664,002 B2 | 3/2014 | Yeung et al. |
| 8,673,218 B2 | 3/2014 | Jaffe et al. |
| 8,679,853 B2 | 3/2014 | Bhullar et al. |
| 8,722,357 B2 | 5/2014 | Baer et al. |
| 8,785,883 B2 | 7/2014 | Nakazawa et al. |
| 8,829,426 B2 | 9/2014 | Vertes et al. |
| 8,936,762 B2 | 1/2015 | Ehrlich et al. |
| 9,314,764 B2 | 4/2016 | Hess et al. |
| 10,227,583 B2 * | 3/2019 | Cochran ............ C12N 15/1055 |
| 2002/0045270 A1 | 4/2002 | Schurenberg et al. |
| 2003/0003500 A1 | 1/2003 | Lafferty et al. |
| 2003/0044968 A1 | 3/2003 | Lafferty et al. |
| 2003/0096220 A1 | 5/2003 | Lafferty et al. |
| 2003/0106997 A1 | 6/2003 | Beecher et al. |
| 2003/0143580 A1 | 7/2003 | Straus et al. |
| 2003/0215798 A1 | 11/2003 | Short et al. |
| 2004/0005582 A1 | 1/2004 | Shipwash |
| 2005/0070005 A1 | 3/2005 | Keller et al. |
| 2009/0042744 A1 | 2/2009 | Wagner et al. |
| 2009/0161100 A1 | 6/2009 | Minot et al. |
| 2011/0124520 A1 | 5/2011 | Love et al. |
| 2011/0294208 A1 | 12/2011 | Allbritton et al. |
| 2012/0021951 A1 | 1/2012 | Hess et al. |
| 2012/0094851 A1 | 4/2012 | Schellenberger et al. |
| 2013/0190206 A1 | 7/2013 | Leonard et al. |
| 2013/0220528 A1 | 8/2013 | Peng et al. |
| 2013/0237443 A1 | 9/2013 | Knebel et al. |
| 2013/0260479 A1 | 10/2013 | Chou et al. |
| 2014/0011690 A1 | 1/2014 | Dimov et al. |
| 2014/0017700 A1 | 1/2014 | Fan et al. |
| 2014/0098214 A1 | 4/2014 | Schlaudraff et al. |
| 2014/0147884 A1 | 5/2014 | Schlaudraff et al. |
| 2014/0272984 A1 | 9/2014 | Hasson et al. |
| 2014/0329240 A1 | 11/2014 | Beer et al. |
| 2014/0329305 A1 | 11/2014 | Brown et al. |
| 2015/0051118 A1 | 2/2015 | Ghenciu et al. |
| 2015/0323544 A1 | 11/2015 | Cambell et al. |
| 2016/0202150 A1 | 7/2016 | Schlaudraff et al. |
| 2016/0245805 A1 | 8/2016 | Baer et al. |

FOREIGN PATENT DOCUMENTS

| | | |
|---|---|---|
| EP | 1207392 | 5/2002 |
| EP | 1963815 | 9/2008 |
| EP | 2733673 | 5/2014 |
| WO | WO 1998/020020 | 5/1998 |
| WO | WO 1999/017094 | 4/1999 |
| WO | WO 2000/031774 | 6/2000 |
| WO | WO 2002/031203 | 4/2002 |
| WO | WO 2005/040406 | 5/2005 |
| WO | WO 2007/035633 | 3/2007 |
| WO | WO 2007/098148 | 8/2007 |
| WO | WO 2008/034833 | 3/2008 |
| WO | WO 2012/007537 | 1/2012 |
| WO | WO 2013/008583 | 1/2013 |
| WO | WO 2013/138767 | 3/2013 |
| WO | WO 2014/008056 | 1/2014 |
| WO | WO 2015/104321 | 1/2015 |
| WO | WO 2016/019341 | 2/2016 |
| WO | WO 2016/116455 | 7/2016 |

OTHER PUBLICATIONS

Chen et al., Nature Chem. Biol. 12:76-81 (2016).

Kelkar et al., Curr. Opin. Pharmacol. 12:592-600 (2012).

Michelini et al., Anal. Bioanal. Chem. 398:227-38 (2010).

Quiagen, www.sabiosciences.com/reporterassay.php (Accessed Apr. 2017).

Quiagen, http://www.sabiosciences.com/reporter_assay_product/HTML/CCS-013L.html (Accessed Apr. 2017).

Guild et al., "Wheat germ cell-free expression system as a pathway to improve protein yield and solubility for the SSGCID pipeline," Acta Cryst., vol. 67, Pt. 9, pp. 1027-1031 (2011).

* cited by examiner

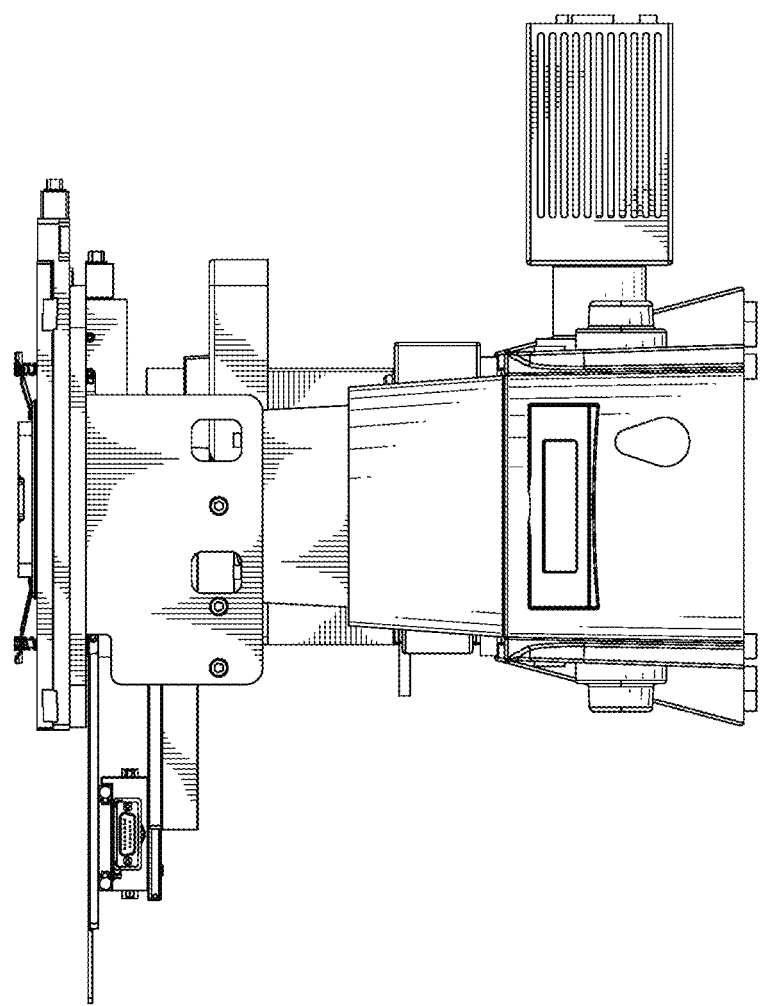

METHODS AND SYSTEMS FOR SCREENING USING MICROCAPILLARY ARRAYS

BACKGROUND OF THE INVENTION

The analysis of biological samples, including the identification, characterization, and re-engineering of proteins, nucleic acids, carbohydrates, and other important biomolecules, has benefited greatly from the scaling up of sample numbers and the scaling down of sample sizes. For example, the two-dimensional microarrays of biological materials, such as DNA microarrays, have enabled the development of high-throughput screening methods involving multiplexed approaches for processing samples and detecting results.

The above approaches have, in some cases, benefited from their combination with optical sensing technology to identify specimens of interest using fluorescent or other corresponding specific and sensitive labeling approaches.

While such techniques provide analytical information about a particular sample, for example the presence and potentially the amount of a particular biomolecule in a solution or the sequence of a particular nucleic acid or polypeptide, they typically do not allow for the recovery of a biological sample identified by the assay without inactivating or otherwise damaging the sample of interest.

There is therefore a continuing need to develop improved microscale screening and analysis methods and systems with high throughput capabilities, and particularly methods and systems that enable recovery of samples identified in the screening and analysis.

SUMMARY OF THE INVENTION

The present disclosure addresses these and other needs by providing in one aspect methods of screening a population of variant proteins comprising the steps of:
  providing a microcapillary array comprising a plurality of microcapillaries, each microcapillary comprising a variant protein, an immobilized target molecule, and a reporter element, wherein the variant protein associates with the immobilized target molecule with a particular affinity; and
  measuring a signal from at least one reporter element that indicates association of at least one variant protein with at least one immobilized target molecule to identify at least one microcapillary of interest.

In some embodiments, the methods further comprise the step of isolating the contents of the microcapillary of interest.

In another aspect are provided systems for screening a population of variant proteins comprising:
  an array comprising a plurality of microcapillaries, each microcapillary comprising a variant protein, an immobilized target molecule, and a reporter element, wherein the variant protein associates with the immobilized target molecule with a particular affinity.

In some embodiments, the systems further comprise a microscope.

In some embodiments, the systems further comprise an optical source and a detector.

In some embodiments, the systems further comprise an extraction device.

In some embodiments, the systems further comprise a two-stage sample recovery element.

BRIEF DESCRIPTION OF THE DRAWINGS

FIGS. 6A-6E are different views of a microscope system designed to carry out the screening methods of the instant disclosure.

DETAILED DESCRIPTION OF THE INVENTION

Figure 1A:
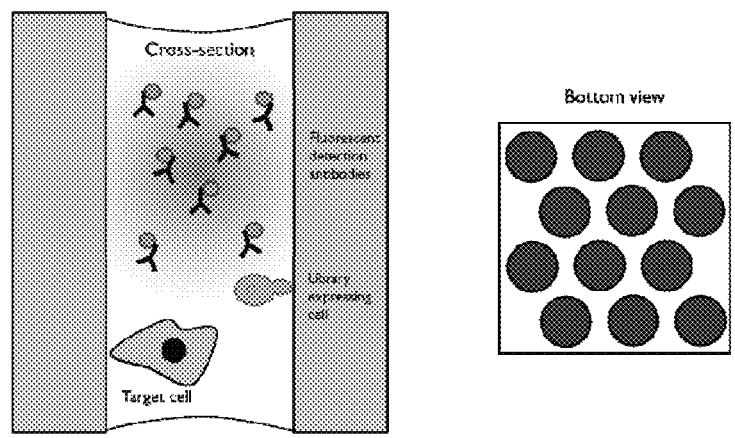
FIGS. 1A-1C schematically illustrate the steps of an exemplary microcapillary screening assay. The illustration on the left in each panel is a cross-sectional view from the side of a single microcapillary. The illustration on the right in each panel is a bottom view of a subsection of the array of microcapillaries. The shading in each case is intended to illustrate an electromagnetic signal, such as fluorescence.

Microcapillary arrays have recently been employed in approaches for high-throughput analysis and protein engineering with large numbers of biological samples, for example in an approach that has been termed "microcapillary single-cell analysis and laser extraction" or "µSCALE". See Chen et al. (2016) Nature Chem. Biol. 12:76-81; DOI: 10.1038/NCHEMBIO.1978. This approach relies on the spatial segregation of single cells within a microcapillary array, and thus enables repeated imaging, cell growth, and protein expression of the separate samples within each microcapillary of the microcapillary array. Accordingly, the technique enables massively parallel, quantitative biochemical and biophysical measurements on millions or multi-millions of samples within a microcapillary array, for example, in the analysis of millions or multi-millions of protein variants expressed from yeast, bacteria, or other suitable cells distributed throughout the array. Advantageously, the approach has allowed the simultaneous time-resolved kinetic analysis of the multiplexed samples, as well as the sorting of those cells based on targeted phenotypic features.

The development of µSCALE methods and apparatus for the quantitative biochemical and biophysical analysis of populations of biological variants has also been reported in U.S. Patent Application Publication No. 2016/0244749 A1, which is incorporated by reference herein in its entirety. Extraction of the contents of a desired microcapillary according to the µSCALE approach requires, however, the inclusion of a radiation-absorbing material in each sample and the directing of electromagnetic radiation from a pulsed laser into this material, thus adding complexity to the extraction methods. In addition, earlier methods of screening of biological variants in arrays of microcavities relied on the addition of microparticles to the arrayed samples to partially or completely inhibit the transmission of electromagnetic radiation into and out of the sample in order to minimize signal emitted from microcavities lacking a desired binding activity. See U.S. Patent Application Publication No. U.S. 2014/0011690 A1. In some aspects of the instant disclosure, the screening methods do not rely on these additional sample components or manipulations, thus simplifying and improving the efficiency of the screening techniques.

In specific applications of these approaches, and as will be disclosed in more detail herein, the target molecule can be immobilized on a surface, such as the surface of a particle (e.g., a magnetic particle), a cell, or a microcapillary wall. The interaction between a variant protein and a target molecule in these approaches can then be measured by several methods, including methods utilizing detectable antibodies and methods of measuring detectable signals generated within the target cells. It will be understood that such methods can be used in high-throughput screens to discover protein variants that bind to target molecules, for example a target molecule on a cell or other surface.

Methods of Screening

Accordingly, in some aspects, the instant disclosure provides methods of screening a population of variant proteins comprising the steps of:

providing a microcapillary array comprising a plurality of microcapillaries, each microcapillary comprising a variant protein, an immobilized target molecule, and a reporter element, wherein the variant protein associates with the immobilized target molecule with a particular affinity; and measuring a signal from at least one reporter element that indicates association of at least one variant protein with at least one immobilized target molecule to identify at least one microcapillary of interest.

In these methods, the microcapillary arrays preferably comprise a plurality of longitudinally fused capillaries, for example fused silica capillaries, although any other suitable material may be utilized in the arrays. See, e.g., PCT International Patent Publication Nos. WO2012/007537 and WO2014/008056, the disclosures of which are incorporated by reference herein in their entireties. Such arrays can be fabricated, for example, by bundling millions or billions of silica capillaries and fusing them together through a thermal process, although other suitable methods of fabrication may also be employed. The fusing process may comprise, for example, the steps of i) heating a capillary single draw glass that is drawn under tension into a single clad fiber; ii) creating a capillary multi draw single capillary from the single draw glass by bundling, heating, and drawing; iii) creating a capillary multi-multi draw multi capillary from the multi draw single capillary by additional bundling, heating, and drawing; iv) creating a block assembly of drawn glass from the multi-multi draw multi capillary by stacking in a pressing block; v) creating a block pressing block from the block assembly by treating with heat and pressure; and vi) creating a block forming block by cutting the block pressing block at a precise length (e.g., 1 mm).

In some embodiments, the fabrication method further comprises slicing the silica capillaries, thereby forming very high-density glass microcapillary arrays. In some embodiments, the microcapillary arrays may be cut to approximately 1 millimeter in height, but even shorter microcapillary arrays are contemplated, including arrays of 10 μm in height or even shorter. In some embodiments, even longer microcapillary arrays are contemplated, including arrays of 10 mm or even longer.

Such processes form very high-density microcapillary arrays that are suitable for use in the present methods. In an exemplary array, each microcapillary has an approximate 5 μm diameter and approximately 66% open space (i.e., representing the lumen of each microcapillary). In some arrays, the proportion of the array that is open ranges between about 50% and about 90%, for example about 60 to 75%, such as a microcapillary array provided by Hamamatsu that has an open area of about 67%. In one particular example, a 10×10 cm array having 5 μm diameter microcapillaries and approximately 66% open space has about 330 million total microcapillaries.

In various embodiments, the internal diameter of each microcapillary in the array ranges from between approximately 1 μm and 500 μm. In some arrays, each microcapillary can have an internal diameter in the range between approximately 1 μm and 300 μm; optionally between approximately 1 μm and 100 μm; further optionally between approximately 1 μm and 75 μm; still further optionally between approximately 1 μm and 50 μm; and still further optionally between approximately 5 μm and 50 μm.

In some microcapillary arrays, the open area of the array comprises up to 90% of the open area (OA), so that, when the pore diameter varies between 1 μm and 500 μm, the number of microcapillaries per cm of the array varies between approximately 460 and over 11 million. In some microcapillary arrays, the open area of the array comprises about 67% of the open area, so that, when the pore size varies between 1 μm and 500 μm, the number of microcapillaries per square cm of the array varies between approximately 340 and over 800,000.

In one particular embodiment, a microcapillary array can be manufactured by bonding billions of silica capillaries and then fusing them together through a thermal process. After that slices (0.5 mm or more) are cut out to form a very high aspect ratio glass microcapillary array. Arrays are also commercially available, such as from Hamamatsu Photonics K. K. (Japan), Incom, Inc. (Massachusetts), Photonis Technologies, S.A.S. (France) Inc., and others. In some embodiments, the microcapillaries of the array are closed at one end with a solid substrate attached to the array.

The microcapillary arrays of the instant screening methods can comprise any number of microcapillaries within the array. In some embodiments, the microcapillary array comprises at least 100,000, at least 300,000, at least 1,000,000, at least 3,000,000, at least 10,000,000, or even more microcapillaries. The number of microcapillaries within an array is preferably chosen in view of the size of the variant protein library to be screened.

As described above, each capillary in the microcapillary arrays used in the instant screening methods comprises a variant protein, an immobilized target molecule, and a reporter element, where the variant protein is one of the population of variant proteins that is being subjected to the screening method. The population of variant proteins can be any population of proteins that can be suitably distributed within a microcapillary array. Ideally, the population of variant proteins is distributed in the microcapillary array so that each microcapillary comprises a small number of different variant proteins, preferably just a single different variant protein per microcapillary. Importantly, the population of variant proteins is chosen in combination with the immobilized target molecule, such that at least some of the proteins in the population can associate with the immobilized target molecule with a particular affinity, such that the association is detectable by measuring a signal from a reporter element.

The term "protein", as used herein, refers both to full-length proteins or polypeptide sequences and to fragments thereof. Such fragments may include fragments that retain a functional activity, such as, for example, a binding activity. The terms "protein" and "polypeptide" are used interchangeably throughout the disclosure and include chains of amino acids covalently linked through peptide bonds, where each amino acid in the polypeptide may be referred to as an "amino acid residue". Use of the terms "protein" or "polypeptide" should not be considered limited to any particular length of polypeptide, e.g., any particular number of amino acid residues. The subject proteins may include proteins having non-peptidic modifications, such as post-translational modifications, including glycosylation, acetylation, phosphorylation, sulfation, or the like, or other chemical modifications, such as alkylation, acetylation, esterification, PEGylation, or the like. Additional modifications, such as the inclusion of non-natural amino acids within a polypeptide sequence or non-peptide bonds between amino acid residues should also be considered within the scope of the definition of the term "protein" or "polypeptide".

The population of variant proteins is preferably a population of proteins having minor variations, for example a population of proteins where each protein has a slightly different amino acid sequence. The screening assays can, therefore, identify variant protein sequences having desirable properties. Because the screens can be performed in such large numbers at microscopic scale, huge numbers of variant proteins can be assayed in relatively short times.

In some embodiments, each microcapillary in the microcapillary array comprises 0 to 5 different variant proteins from the population of variant proteins. In specific embodiments, each microcapillary in the microcapillary array comprises 0 to 4, 0 to 3, 0 to 2, or even 0 to 1 different variant proteins from the population of variant proteins. It should be understood that the different variant proteins in the population of variant proteins differ in their molecular structure, whether the difference is in their amino acid sequence or in some other chemical modification of the protein.

It should be understood that each microcapillary will typically comprise many multiple copies of the same variant protein, depending on the source and expression level of the particular variant protein (see below). In some embodiments, each microcapillary will comprise thousands, tens of thousands, hundreds of thousands, millions, billions, or even more molecules of a particular variant protein, depending on how the variant protein is delivered to or expressed within the microcapillary.

The population of variant proteins is typically generated using a genetic library in a biological expression system, for example in an in vitro (i.e., cell-free) expression system or in an in vivo or cellular expression system. Exemplary cellular expression systems include, for example, animal systems (e.g., mammalian systems), fungal systems (e.g., yeast systems), bacterial systems, insect systems, or plant systems. In specific embodiments, the expression system is a mammalian system or a yeast system. The expression system, whether cellular or cell-free, typically comprises a library of genetic material encoding the population of variant proteins. Cellular expression systems offer the advantage that cells with a desirable phenotype, for example cells that express a particular variant protein of interest, such as a variant protein capable of associating with an immobilized target molecule with high affinity, can be grown and multiplied, thus facilitating and simplifying the identification and characterization of the proteins of interest expressed by the cells.

Genetic libraries encoding large populations of variant proteins are well known in the art of bioengineering. Such libraries are often utilized in systems relying on the process of directed evolution to identify proteins with advantageous properties, such as high-affinity binding to target molecules, stability, high expression, or particular spectroscopic, e.g., fluorescence, or enzymatic activities. Often the libraries include genetic fusions with sequences from the host expression system, for example fragments of proteins directing subcellular localization, where the expressed population of variant fusion proteins are directed by the targeting fragment to a particular location of the cell or virus particle for purposes of activity screening of the variant protein population. Large numbers of variant proteins (e.g., $10^6$ variants, $10^8$ variants, $10^{10}$ variants, $10^{12}$ variants, or even more variants) can be generated using routine bioengineering techniques, as is well known in the art.

Accordingly, in some embodiments, the variant proteins are soluble proteins, for example soluble proteins that are secreted by a cellular expression system. Exemplary soluble variant proteins include antibodies and antibody fragments, alternative protein scaffolds, such as disulfide-bonded peptide scaffolds, extracellular domains of cell-surface receptor proteins, receptor ligands, such as, for example, G-protein coupled receptor ligands, other peptide hormones, lectins, and the like. Advantageously, the variant proteins screened for binding activity in the instant methods do not need to be covalently attached to the cell or virus that expresses them in order to be identified following a screening assay, since a variant protein with a desired binding activity and the cell that expressed it remain co-localized within the same microcapillary throughout the assay. Isolation of the contents of the desired microcapillary, followed by propagation of the cell or virus clone responsible for expression of the desired variant protein, thereby enables the identification and characterization of that protein. Unlike screening assays where a variant protein of interest is displayed by fusion of the protein to a molecule on the surface of a cell or virus particle, the variant proteins identified in the instant screening methods need not be altered in any way following their identification. The observed activities of the variant proteins in the screens are thus more likely to represent the actual activities of those proteins in their subsequent applications.

In other embodiments, however, it may be desirable for the variant proteins to be membrane-associated proteins, for example proteins remaining associated with the surface of a cell or a viral particle in an expression system. Screening of cell-associated variant proteins may be desirable where the variant protein and its target molecule mediate interactions between two cells within a biological tissue. The ability to screen against cell-associated variant proteins may also be desirable in screening for interactions with traditionally "non-druggable" protein targets, such as, for example, G-protein coupled receptors or ion channels.

In addition to a variant protein, each microcapillary in the microcapillary arrays of the instant screening methods also comprises an immobilized target molecule. The immobilized target molecule serves as the potential binding partner for the variant protein of the screening assay. Unlike the population of variant proteins, where each microcapillary ideally contains a variant protein of slightly different sequence, the immobilized target molecules ideally have the same molecular structure in each microcapillary of the array.

In some embodiments, the target molecule is a target protein or polypeptide, a target nucleic acid, a target carbohydrate, a target lipid, or a combination of two or more of these target molecules. For example, in some embodiments the target molecule can be a lipid-modified or glycosylated protein. In some embodiments, the target molecule is immobilized on a surface. In more specific embodiments, the target molecule is immobilized on the surface of a cell, such as a target cell, the surface of a bead, the surface of a microcapillary wall, or another suitable surface. In other more specific embodiments, the target molecule is a native protein, for example a native protein immobilized on the surface of a cell. In still other more specific embodiments, the target molecule is immobilized on a surface configured to settle in the microcapillary by gravitational sedimentation.

As previously noted, in the methods of the instant disclosure, the variant protein associates with the immobilized target molecule with a particular affinity within a microcapillary. Importantly, such affinities should be sufficiently strong for variant proteins of interest that the association can be measured by a signal from a reporter element. Binding affinities are typically assessed by a dissociation constant ($K_d$), as is well understood by those of ordinary skill in the art, where the lower the dissociation constant, the higher the affinity. In some embodiments, the association between the variant protein of interest and the immobilized target molecule displays a dissociation constant in the millimolar to micromolar range. In specific embodiments, the association displays a dissociation constant from micromolar to high nanomolar (i.e., $10^{-6}$ M to $10^{-8}$ M). In more specific embodiments, the association displays a dissociation constant from lower nanomolar to high picomolar (i.e., $10^{-8}$ M to $10^{-10}$ M). In even more specific embodiments, the association displays a dissociation constant in the picomolar range (i.e., $10^{-10}$ M to $10^{-12}$ M), or even lower.

In addition to a variant protein and an immobilized target molecule, each microcapillary in the microcapillary array of the instant screening methods also comprises a reporter element. Importantly, the reporter element provides a measurable signal indicative of the association of a variant protein with an immobilized target molecule and thus serves to identify a microcapillary containing variant proteins of interest.

In some embodiments, the reporter element is a labeled antibody or other molecule capable of binding to each variant protein in the population of variant proteins. More specifically, the reporter element is a fluorescently-labeled antibody or other binding molecule.

In some embodiments, the labeled antibody is a labeled primary antibody or a labeled secondary antibody. For purposes of this disclosure, a primary antibody is typically considered to be an antibody that binds directly to an antigen of interest, whereas a secondary antibody is typically considered to be an antibody that binds to a constant region on a primary antibody for purposes of labeling the primary antibody. Accordingly, secondary antibodies are frequently labeled with fluorophores or other detectable labels or are labeled with enzymes that are capable of generating detectable signals. They are generally specific for a primary antibody from a different species. For example, a goat or other animal species may be used to generate secondary antibodies against a mouse, chicken, rabbit, or nearly any primary antibody other than an antibody from that animal species, as is understood by those of ordinary skill in the art. In specific embodiments, the labeled antibody is a fluorescent antibody or an enzyme-linked antibody.

Figure 1B:
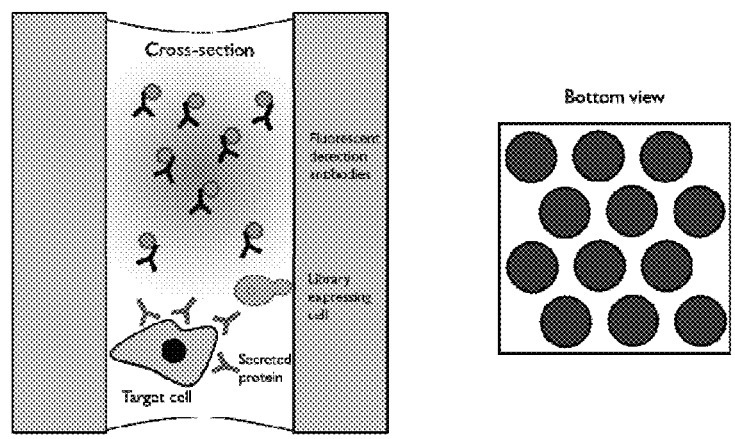
Figure 1C:
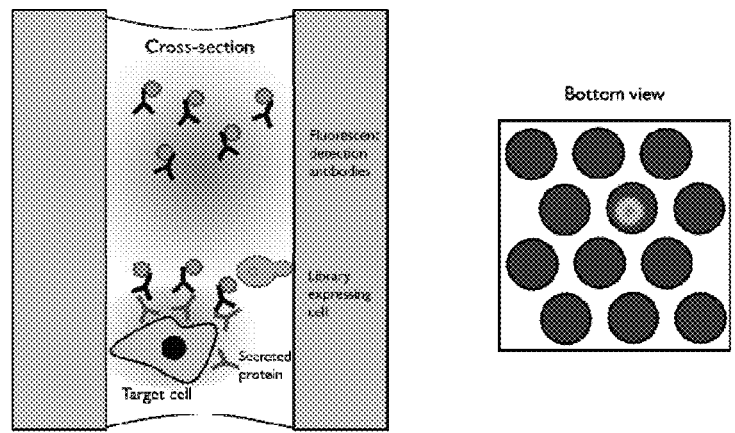

In some of the method embodiments, for example in the screening methods illustrated in FIGS. 1A-1C, the variant protein mediates the association of a reporter element with a target molecule, in this example, a target molecule on the surface of a target cell. As shown in FIG. 1B, where the variant protein (here designated as a "secreted protein") has sufficient affinity for its target molecule on the target cell that the variant proteins associate with the target cell under the conditions of the microcapillary solution. The reporter element (here designated as "fluorescent detection antibodies") binds to the variant protein, ideally at an epitope that does not affect the affinity of the variant protein for the target molecule, as shown in FIG. 1C.

As would be understood by those of ordinary skill in the art, when a soluble reporter element, such as a fluorescent antibody, is used in the instant screening methods, the signal emitted by any excess reporter element remaining free in solution (i.e., either not bound to a variant protein or bound to a variant protein that is not bound to a target molecule) within the microcapillary should not be so high that it overwhelms the signal of reporter elements associated with a target molecule via a variant protein (see, e.g., the unassociated fluorescent detection antibodies illustrated in FIG. 1C). Such background signals can be minimized, however, by limiting the concentration of labeled antibody or other reporter element within the microcapillary solution. In addition, where signals from the screening methods are measured using a fluorescent microscope, configuring the microscope to image a relatively narrow depth of field bracketing the location of the target molecules (e.g., the bottom of the microcapillaries when target cells have settled there by gravitational sedimentation) can minimize the background signal from reporter elements not associated with the target molecule.

In other embodiments, the reporter element is an intracellular reporter element that generates a detectable signal in connection with a binding event, such as, for example, the association of a variant protein with an immobilized target molecule, for example, a receptor or other target molecule on the surface of the cell. In these embodiments, the reporter element may comprise an entire cellular pathway, such as, for example, an intracellular signaling pathway. Such a pathway should include, or be engineered to include, a detectable signal as the downstream readout of the pathway. In contrast to the assays illustrated in FIGS. 1A-1C, where the detectable signal is bound to the outer surface of the target cell, the detectable signal in these embodiments would typically be generated inside the target cell.

Many intracellular signaling pathways have been developed for use in high throughput screening assays, in particular in drug discovery screens, and can be adapted for use in the instant assays. See, e.g., Michelini et al. (2010) *Anal. Bioanal. Chem.* 398:227-38. In particular, any cellular assay where a binding event with a target molecule on the surface of a cell results in the generation of a measurable signal, in particular a fluorescent signal, can be used as a reporter element in the instant assays. Preferably, the cells can be engineered to express a target molecule of interest on their surface, so that the binding of a particular variant protein to the target molecule and the consequent activation of the intracellular signaling pathway result in the production of a detectable signal from the reporter element, thus enabling the identification of the microcapillary as a positive hit. The expression of a green fluorescent protein (GFP), or any of a wide variety of variant fluorescent proteins, is often used as a readout in such cellular assays and can serve as the reporter element endpoint in the instant methods. Alternatively, the signaling readout can be provided by luciferase or other related enzymes that produce bioluminescent signals, as is well understood by those of ordinary skill in the art. See, e.g., Kelkar et al. (2012) *Curr. Opin. Pharmacol.* 12:592-600. Other well-known enzymatic reporters from bacterial and plant systems include β-galactosidase, chloramphenicol acetyltransferase, β-glucuronidase (GUS), and the like, which can be adapted for use in the instant screening assays with suitable colorogenic substrates. Transcriptional reporters using firefly luciferase and GFP have been used extensively to study the function and regulation of transcription factors. They can likewise be adapted for use in the instant screening assays. Exemplary intracellular signaling systems are available commercially, for example the Cignal™ Reporter Assay kits from Qiagen (see, e.g., www.sabiosciences.com/reporterassays.php), which are available with either luciferase or GFP readouts. Such systems can be suitably re-engineered for use in the instant screening methods.

It should be understood that a variant protein expression system, in particular where the expression system is a cellular expression system, can be combined with the immobilized target molecule and the reporter element (or suitable components, such as cellular components, responsible for generating the immobilized target molecule and/or reporter element) prior to the expression of the variant proteins and/or prior to delivery of an assay mixture into the array of microcapillaries. Such approaches advantageously allow for flexibility and control in the timing of interactions between the components compared to prior art microcapillary screening systems, where all of the components of the screening assays are typically mixed and loaded into the microcapillaries in static form. In contrast, the instant methods enable some or all of the components of a binding assay to be generated in situ within the microcapillaries, either by allowing for the growth of cellular components, the expression of genetic components, or both.

It should also be understood that the concentrations of each component of the screening assay within a microcapillary, including the concentration of the variant protein, the concentration of the immobilized target molecule, and the concentration of the reporter element, can be modulated as desired in an assay in order to achieve an optimal outcome. In particular, it may be desirable to modulate the concentration of variant protein and/or immobilized target molecule to achieve the desired level of association between these components. The level of association will also depend on the particular affinity between these components, wherein a higher affinity results in a higher level of association for a given concentration of the components, and a lower affinity results in a lower level of association of the components for a given concentration. Concentration of the reporter element may likewise be modulated in order to achieve optimum levels of signal output, as would be understood by those of ordinary skill in the art.

In some embodiments, each microcapillary in the microcapillary arrays of the instant screening methods further comprises an agent or agents to improve viability of the cellular expression system. Specifically, the agent or agents is included to prevent cell damage during the step of isolating the contents of the microcapillary of interest, for example by a laser pulse (see below). In preferred embodiments, the agent is methylcellulose (for example at 0.001 to 10 wt %), dextran (for example at 0.5 to 10 wt %), pluronic F-68 (for example at 0.01 to 10 wt %), polyethylene glycol ("PEG") (for example at 0.01 to 10 wt %), polyvinyl alcohol ("PVA") (for example at 0.01 to 10 wt %), or the like. Alternatively, or in addition, each microcapillary in the microcapillary arrays of the instant screening methods can further comprise a growth additive, such as, for example, 50% conditioned growth media, 25% standard growth media, or 25% serum. In some embodiments, the conditioned growth media is conditioned for 24 hours. In some embodiments, the added agent is insulin, transferrin, ethanolamine, selenium, an insulin-like growth factor, or a combination of these agents or any of the agents recited above.

The screening methods of the instant disclosure preferably include the further step of measuring a signal from at least one reporter element that indicates association of at least one variant protein with at least one immobilized target molecule to identify at least one microcapillary of interest. In some embodiments, the signal measured is a fluorescent signal, an absorbance signal, a bright-field signal, a dark-field signal, a phase contrast signal, or the like. Accordingly, the measuring step can be performed by an appropriate detector device, for example a device capable of detecting electromagnetic radiation or any other suitable signal. In specific embodiments, the measuring step is performed by a microscope, such as a fluorescence microscope or any other microscope configured to detect the above-mentioned signals.

It should be understood that in preferred embodiments, the microcapillaries utilized in the instant screening methods do not comprise microparticles capable of inhibiting the transmission of electromagnetic radiation. In other words, the microcapillaries are preferably fully transparent to electromagnetic radiation incident on the microcapillary array, in particular along the longitudinal axes of the microcapillaries. In other preferred embodiments, the microcapillaries of the instant screening methods do not comprise magnetic microparticles or beads. In still other preferred embodiments, the microcapillaries of the instant screening methods do not comprise microparticles capable of inhibiting the transmission of electromagnetic radiation, magnetic microparticles, or magnetic beads.

In other preferred embodiments, the microcapillaries utilized in the instant screening methods do not comprise an electromagnetic radiation absorbent material. It should be understood, however, that the component of a reporter element responsible generating a measurable signal in the screening method, for example the fluorophore on a fluorescent antibody, should not be considered an electromagnetic radiation absorbent material for purposes of this aspect of the invention.

In some embodiments, the instant screening methods further comprise the step of isolating the contents of the microcapillary of interest. In specific embodiments, the contents of the microcapillary of interest are isolated by pulsing the microcapillary of interest with a laser. More specifically, the laser can be a diode laser or a diode-pumped Q-switched Nd:YLF laser. In some embodiments, the laser can be directed at the water-glass interface between the microcapillary wall and the sample contained in the microcapillary. Without intending to be bound by theory, it is believed that firing a UV laser at this interface can break the meniscus/water surface tension that normally holds a sample in the microcapillary, thus allowing the sample to fall out of the array via the force of gravity. In other embodiments, the contents of the microcapillary of interest are isolated by laser-triggered vapor force expansion. In some embodiments, the contents of the microcapillary are isolated by breaking the glass of the microcapillary itself.

Systems for Screening

According to another aspect of the invention are provided systems for screening a population of variant proteins comprising:

an array comprising a plurality of microcapillaries, each microcapillary comprising a variant protein, an immobilized target molecule, and a reporter element, wherein the variant protein associates with the immobilized target molecule with a particular affinity. The components of these screening devices are described in detail above.

In some embodiments, the screening systems further comprise an optical source and a detector. The optical source and detector are chosen according to the particular reporter element used in the screening system. For example, where the reporter element generates a fluorescent signal, the optical source provides excitation light of an appropriate wavelength to excite the fluorescent probe. Likewise, the detector is chosen to be sensitive to the wavelength of light emitted by the fluorescent probe. The optical source and the detector may, for example, be components of a microscope, such as a fluorescent microscope, or they may be separate devices, as would be understood by those of ordinary skill in the art.

In some embodiments, the screening system further comprises an extraction device, for example a diode laser, a diode-pumped Q-switched laser, or other appropriate component for isolating the contents of a microcapillary of interest.

Figure 6A:
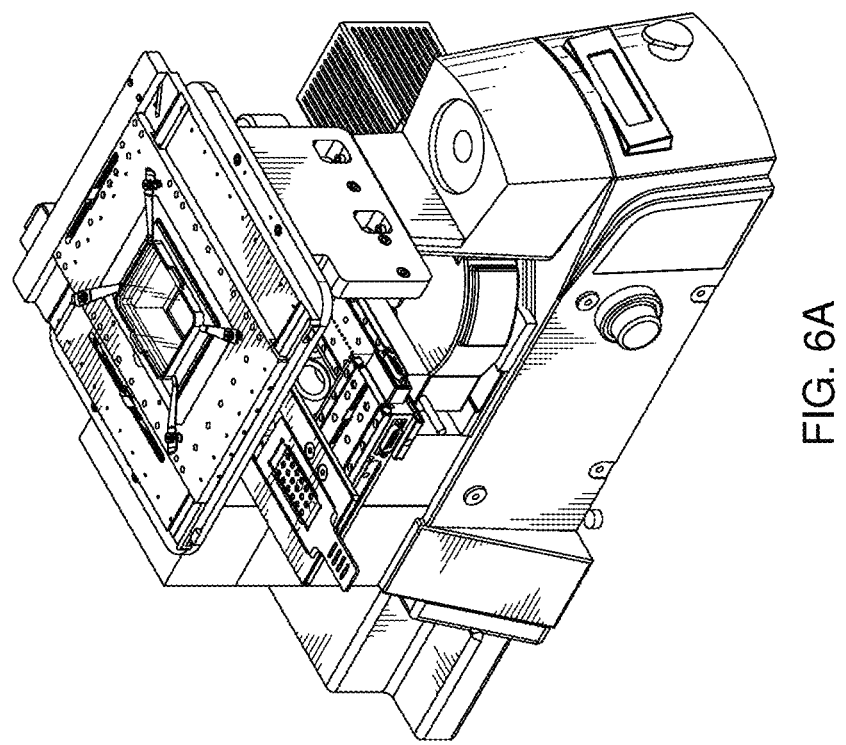
Figure 6C:
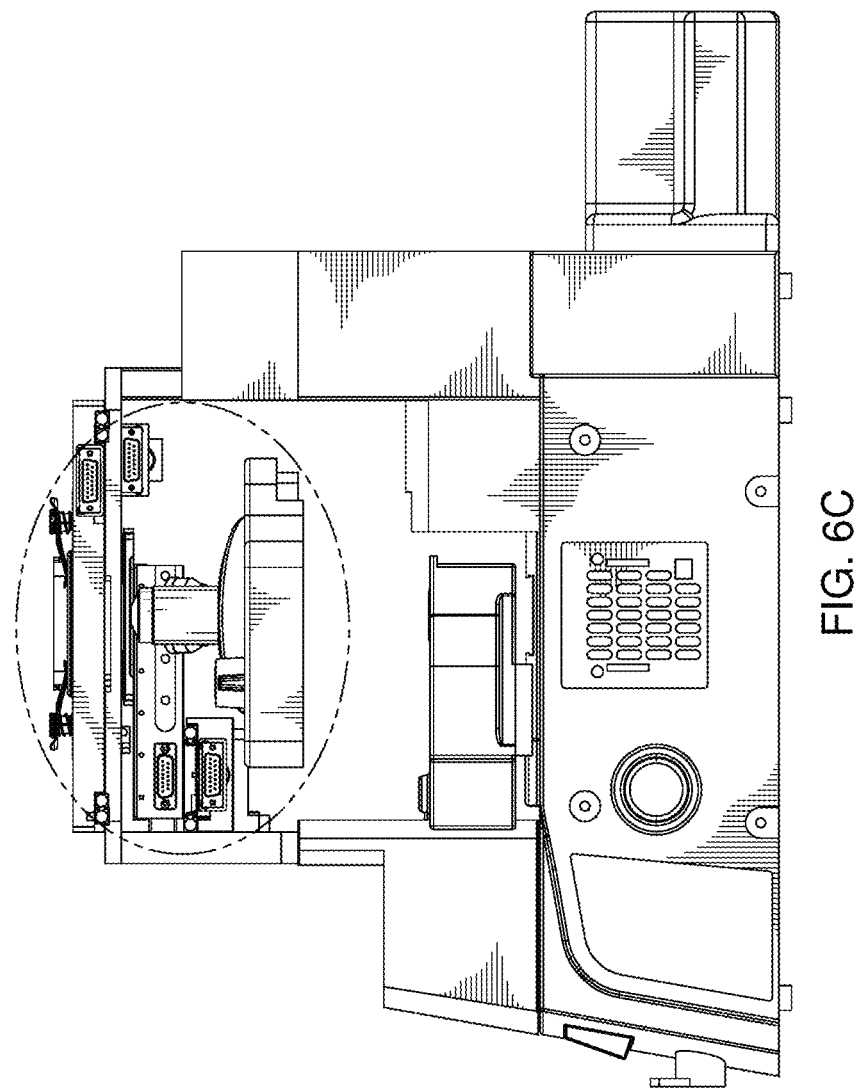
Figure 6D:
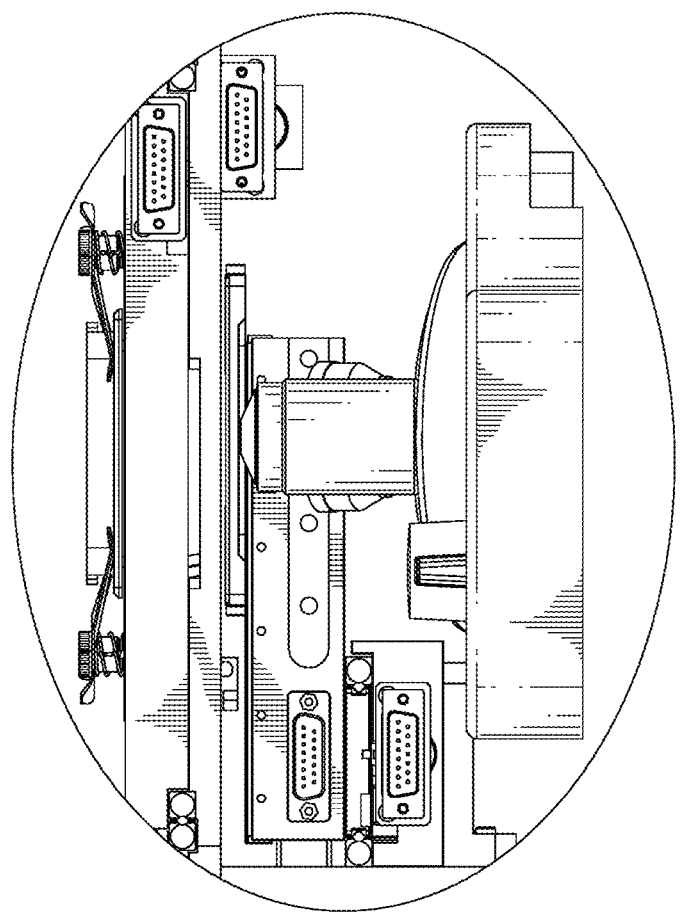
Figure 6E:
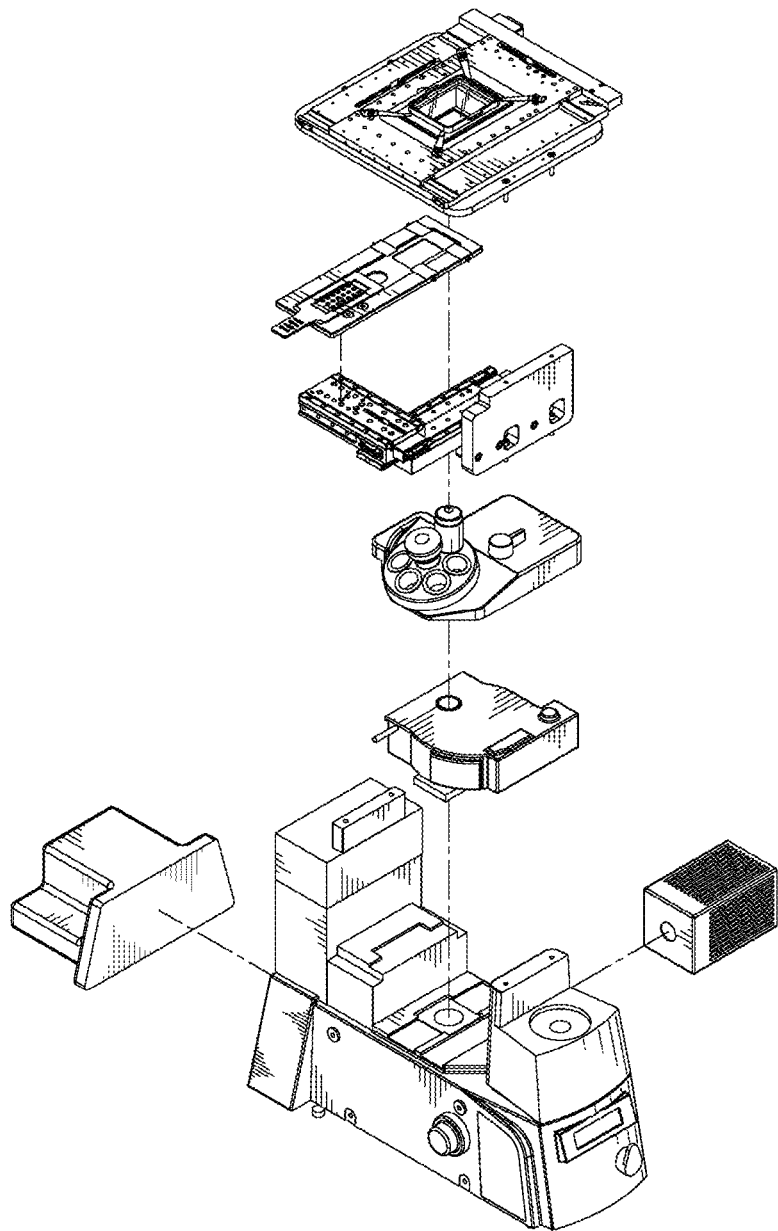

An exemplary microscope for screening populations of variant proteins according to the instant methods is illustrated in the drawings of FIGS. 6A-6E. FIG. 6A shows a perspective view from above the microscope, illustrating both the array-holding stage and the sample-recovery stage. FIG. 6B shows a front view of the device. FIG. 6C shows a view from the right side. A magnified view of the right side of the device is provided in FIG. 6D, which illustrates in detail the relationship between the array-holding stage and the sample-recovery stage. FIG. 6E provides an exploded view of various components of a multi-stage sample-recovery microscope suitable for use in the instant screening systems.

It will be readily apparent to one of ordinary skill in the relevant arts that other suitable modifications and adaptations to the methods and applications described herein can be made without departing from the scope of the invention or any embodiment thereof. Having now described the present invention in detail, the same will be more clearly understood by reference to the following Examples, which are included herewith for purposes of illustration only and are not intended to be limiting of the invention.

EXAMPLES

Example 1. Screening for a Secreted EGFR-Binding Protein

FIG. 1A-FIG. 1C illustrate an exemplary screening method for a soluble protein capable of associating with a cell-surface protein (e.g., the epidermal growth factor receptor ("EGFR")) as the immobilized target molecule, in this case an immobilized target protein. FIG. 1A (left panel) shows the target cell, which expresses EGFR on its surface. Also shown is a "library expressing cell", which expresses a population of variant proteins, and a number "fluorescent detection antibodies" in the microcapillary solution. A bottom view of the microcapillary array is illustrated in the right panel.

Components of Each Microcapillary According to this Screening Assay:
1. Cells secreting the variant protein of interest (the "library expressing cell"). The variant protein of interest is preferably a member of a population of variant proteins, i.e., a protein library.
2. Target protein immobilized on a surface of a "target cell". In this example, the target protein is a native, cell-surface receptor (i.e., EGFR). Alternatively, however, the target protein could be immobilized on another surface, such as a bead surface or a surface of the microcapillary itself.
3. Reporter element
   a. In this example, the reporter element corresponds to a fluorescently-labeled antibody specific for the secreted protein (i.e., the "fluorescent detection antibodies"). The antibody specifically localizes to an epitope on the secreted protein but ideally does not interfere with the binding of the secreted protein to the target protein on the target cell.
   b. Alternatively, the reporter element can be a signaling pathway within the cells that express the target protein. If a secreted variant protein binds the target protein on the cell surface and activates the signaling pathway within the target cell, the binding interaction will generate a fluorescent signal within the cell (not shown).
4. Reaction buffer:
   a. Can be media for the library-expressing cells or for the target cells.
   b. Can be a mammalian imaging solution.

Illustration of Method:
Step 1: Add all components into microcapillary (see FIG. 1A).
Step 2: A specific "secreted protein" is expressed by the library-expressing cell into the microcapillary. Secreted protein variants capable of binding to the target protein are localized to the target cell surface as shown (see FIG. 1B).
Step 3: Fluorescent detection antibodies associated with the bound secreted protein variants are observed in association with target cells in specific microcapillaries (see FIG. 1C).

Detailed Description and Sample Data:
To demonstrate this method, a yeast vector library expressing a protein designed to bind to EGFR on human cancer cells was created. In this library, some yeast variants were capable of expressing the protein, while other variants were not able to express the protein. Yeast cells, cancer cells, and a fluorescent antibody against the expressed protein were added to the microcapillary. After 18 hours, the microcapillary array was imaged. Further details and results of the screen are provided in Example 3 below.

Example 2. Hybridoma Screening Against Mammalian Cells

General Background
Current methods to screen binding interactions between proteins or other target molecules typically rely on the use of "display" methods, e.g., phage display, bacterial display, yeast display, mammalian display, or virus display. In the display methods, a library of genes encoding protein variants is expressed at the surface of the cell or phage. The protein variants are incubated with a soluble version of the target molecule in order to identify protein variants capable of binding to the target. The library can be screened by panning or by fluorescence-activated cell sorting ("FACS"). Such assays have two primary limitations: 1) the engineered protein is typically tethered to the display platform; and 2) it is usually advantageous for a soluble form of the target molecule to exist. Therefore, it can be difficult to develop reliable assays for variant proteins that bind to many target molecules, in particular membrane proteins, such as G-protein coupled receptors and other such receptors.

Hybridoma Screening Against Mammalian Cells
To identify antibody variants with specific binding to a target molecule, hybridomas (which secrete antibody variants)

were added to a cancer cell line that expresses high levels of EGFR as the target molecule. Labeled antibodies specific for the secreted antibodies were then added.

Materials:
Cells:
Mouse hybridoma
A431 target cells (human cancer cell line expressing high levels of EGFR)
Detection antibodies:
Anti-mouse secondary antibody labeled with Alexa488 (a fluorophore)
Media for cell culture:
DMEM-10% fetal bovine serum
DMEM-10% horse serum Cell Line Growth and Preparation.

Mouse hybridoma cells were cultured in complete media (Dulbecco's Modified Eagle's Medium with 10% horse serum). The hybridoma cells were washed twice with PBSA and suspended in complete media at 600 cells/uL. The A431 cells were cultured in complete media (Dulbecco's Modified Eagle's Medium with 10% fetal bovine serum). The A431 cells were washed twice with PBSA and stained with a LiveGreen fluorescent signal. The A431 cells were then suspended in the complete media containing hybridoma at a final concentration of 1800 cells/uL.

Assay Setup.

Following mixing of the two cell types, detection antibodies were added to the reaction mixture: 1:100 dilution of secondary (anti-mouse Alexa488). This reaction mixture was then loaded into an ethanol-sterilized, corona-treated microcapillary array (40 μm diameter, 1 mm thick). A 2 mm slab of 1% weight/volume agarose was placed on the array to help prevent evaporation. After each hour, the sample was imaged under fluorescence and bright-field microscopy.

Figure 2A:
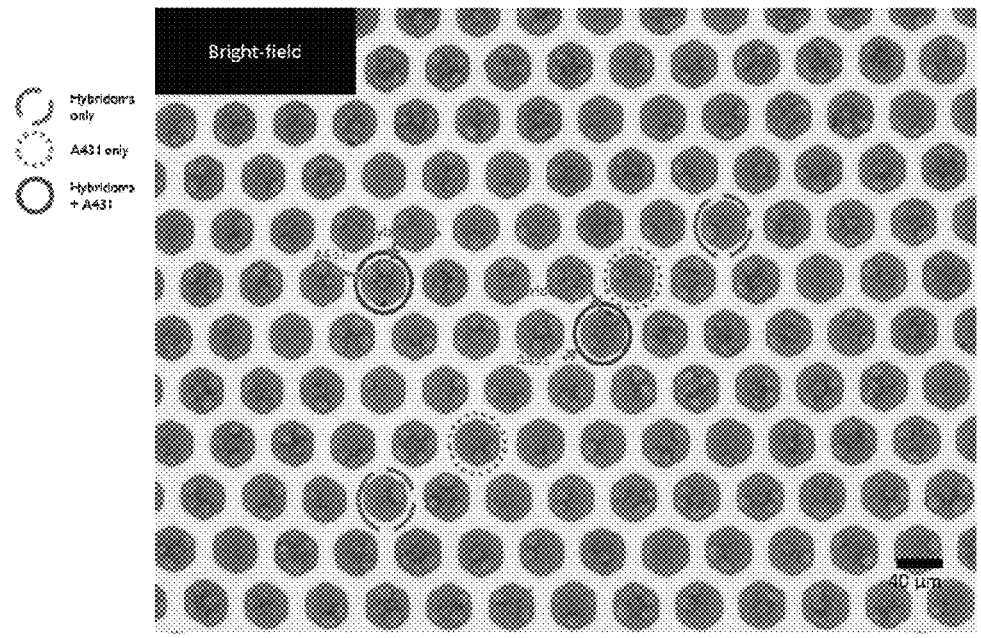
FIGS. 2A-C show the bottom view of a subsection of a microcapillary array illustrating hybridoma screening against mammalian cells, where the cells are imaged using either bright-field (FIG. 2A), LiveGreen (FIG. 2B), or a fluorescent anti-mouse secondary antibody (FIG. 2C).
Figure 2B:
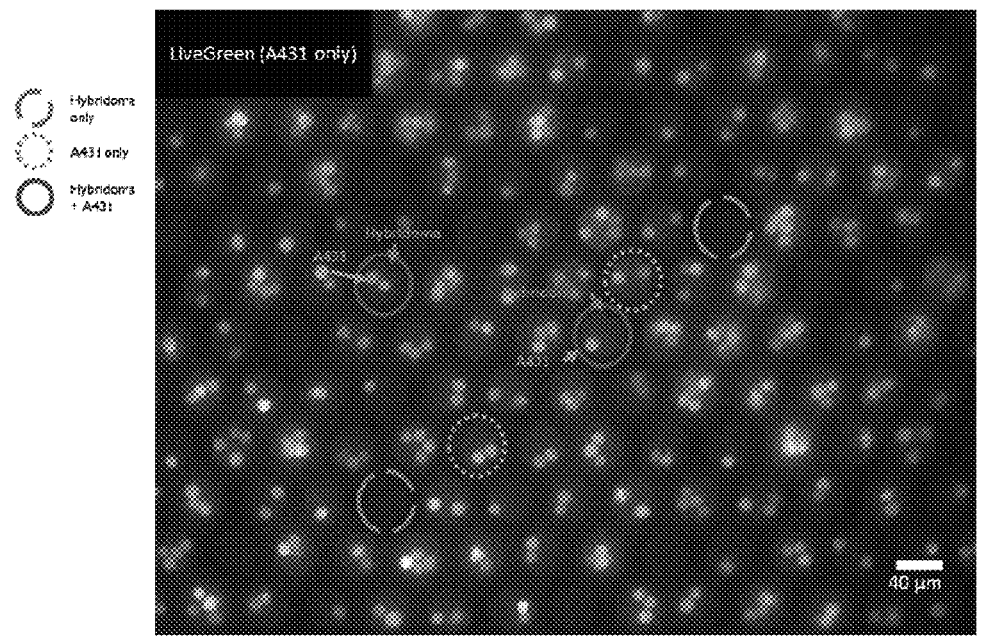
Figure 2C:
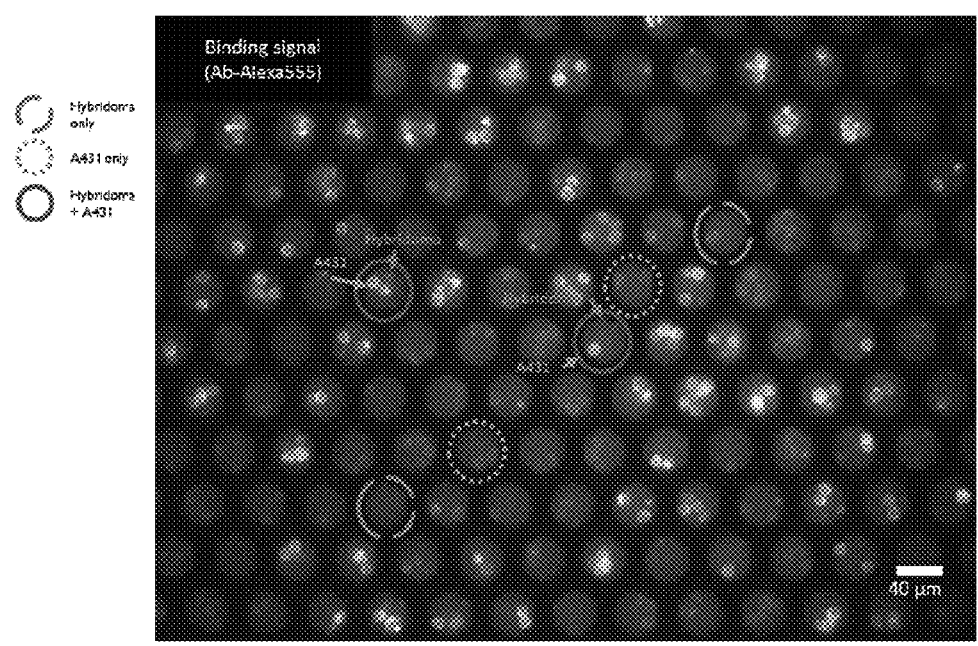

Sample Data:

FIGS. 2A-2C show images of a subsection of the microcapillary array showing either all of the cells (FIG. 2A, bright-field signal), A431 target cells (FIG. 2B, LiveGreen signal), or cells labeled with the fluorescent anti-mouse secondary antibody (FIG. 2C, Ab-a555 signal). Microcapillaries containing hybridoma cells that express antibodies specific for EGFR are indicated with two arrows in each image.

Figure 3:
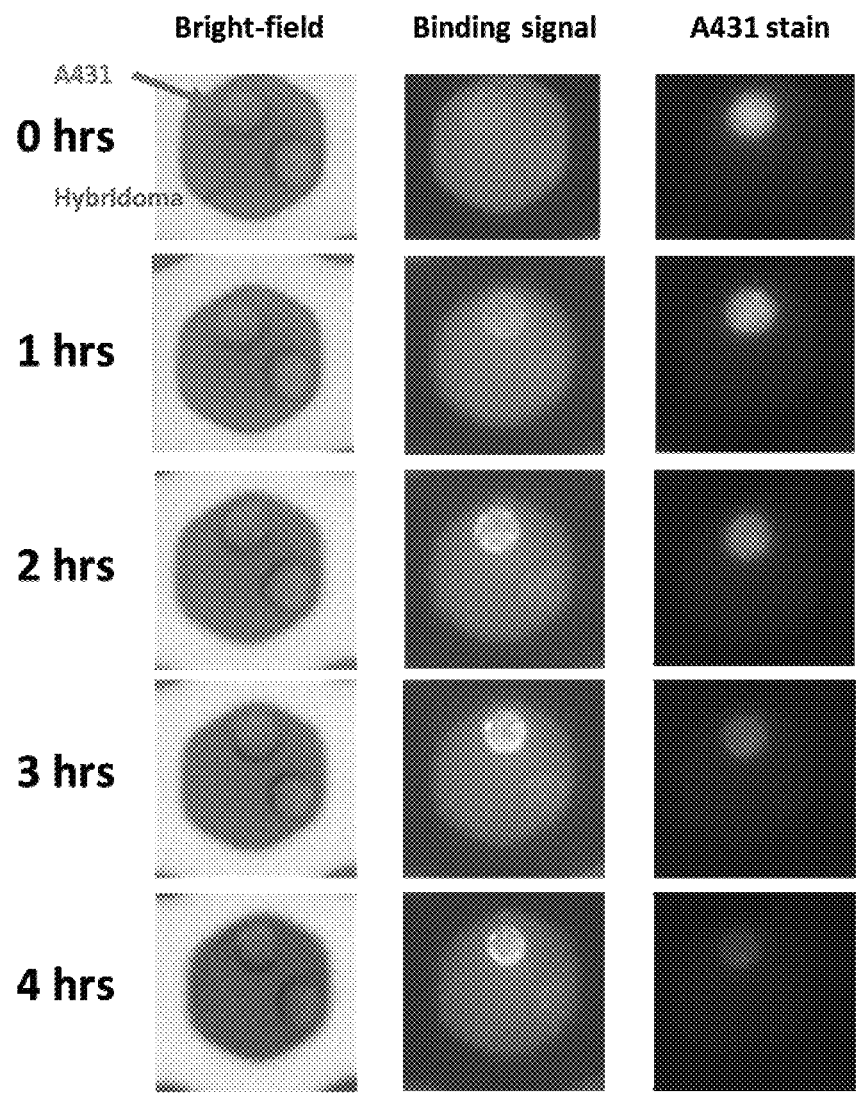
FIG. 3 shows images of a microcapillary containing both an A431 target cell and a hybridoma cell over the course of a 4 hour incubation.

FIG. 3 shows images of a microcapillary containing both an A431 target cell and a hybridoma cell over the course of a 4 hour incubation, where the antibody binding signal to the A431 target cells increased during the time course of the assay as mouse antibodies specific to EGFR are produced (middle column). LiveGreen staining of the A431 target cells declined over the same time period (right column).

Example 3. Yeast Library Screening Against Mammalian Cells

To determine the best secretion yeast plasmid vectors, a yeast vector library expressing scaffold proteins designed to bind to EGFR on a cancer cell surface was created. This library contained yeast cells with various soluble expression levels of a scaffold protein. Using the described assay, the variant expression library was screened to recover the plasmid vectors with high expression of the desired scaffold protein. In this experiment, the secreted scaffold has a c-Myc tag, which can be labeled with fluorescently-labeled antibodies.

Materials:
Cells:
Yeast secretion library of scaffold proteins
A431 cells (human cancer cell line expressing high levels of EGFR)
Detection antibodies:
Chicken anti-c-Myc
Anti-chicken secondary antibody labeled with Alexa488
Media for cell culture:
DMEM-10% FBS
SD-CAA minimal yeast media
Reaction buffer:
SD-CAA minimal yeast media Methods:

Cell Line Growth and Preparation.

The yeast library was grown in SD-CAA minimal yeast media (20 g dextrose; 6.7 g Difco yeast nitrogen base; 5 g Bacto casamino acids; 5.4 g $Na_2HPO_4$; 8.56 g $NaH_2PO_4.H_2O$; dissolved in deionized $H_2O$ to a volume of 1 liter). After growth, the yeast cells were washed twice with PBSA (phosphate-buffered saline+1 mg/ml BSA) and suspended in SD-CAA at a final concentration of 2,400 cells/uL.

The A431 cells were cultured in complete media (Dulbecco's Modified Eagle's Medium with 10% fetal bovine serum). The A431 cells were washed twice with PBSA and suspended in the SD-CAA containing yeast cells at a final concentration of 600 cells/uL.

Assay Setup.

Following mixing of the two cell types, two antibodies were added to the reaction mixture: 1:250 dilution of an unlabeled primary antibody (chicken anti-c-Myc) and 1:200 dilution of a labeled secondary antibody (anti-chicken Alexa488). This reaction mixture was then loaded into an ethanol-sterilized, corona-treated microcapillary array (40 μm diameter, 1 mm thick). A 2 mm slab of 1% weight/volume agarose was placed on the array to help prevent evaporation. After 18 hours of growth, the sample was imaged under fluorescence and bright-field microscopy.

Microcapillary Array Extraction.

A Triton UV laser was used to extract the contents of desired capillaries. The laser operates for 18±2 ms (n=5 measurements), delivering a train of pulses at 2.5 kHz with a total energy of approximately 100 μJ. The microcapillary contents were extracted onto a glass coverslip, which was then placed in yeast growth media (liquid medium or agar plates) to propagate the extracted cells.

Sample Data

Figure 4A:
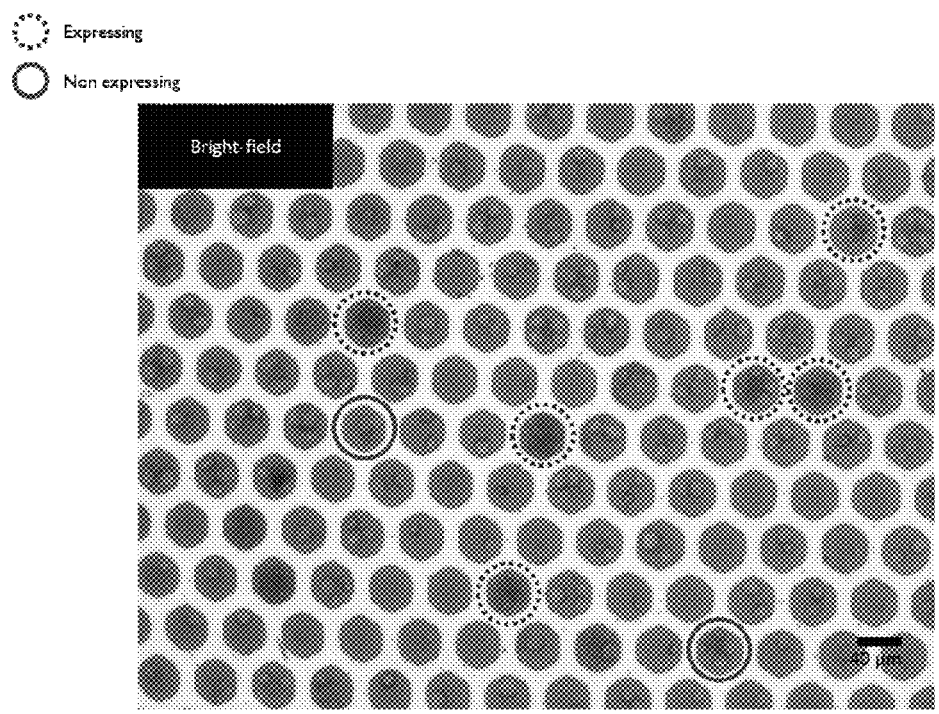
FIGS. 4A and 4B show images of a subsection of a microcapillary array highlighting expressing and non-expressing yeast cells against mammalian cells, where the cells are imaged using either bright-field (FIG. 4A) or a fluorescent antibody (FIG. 4B)
Figure 4B:
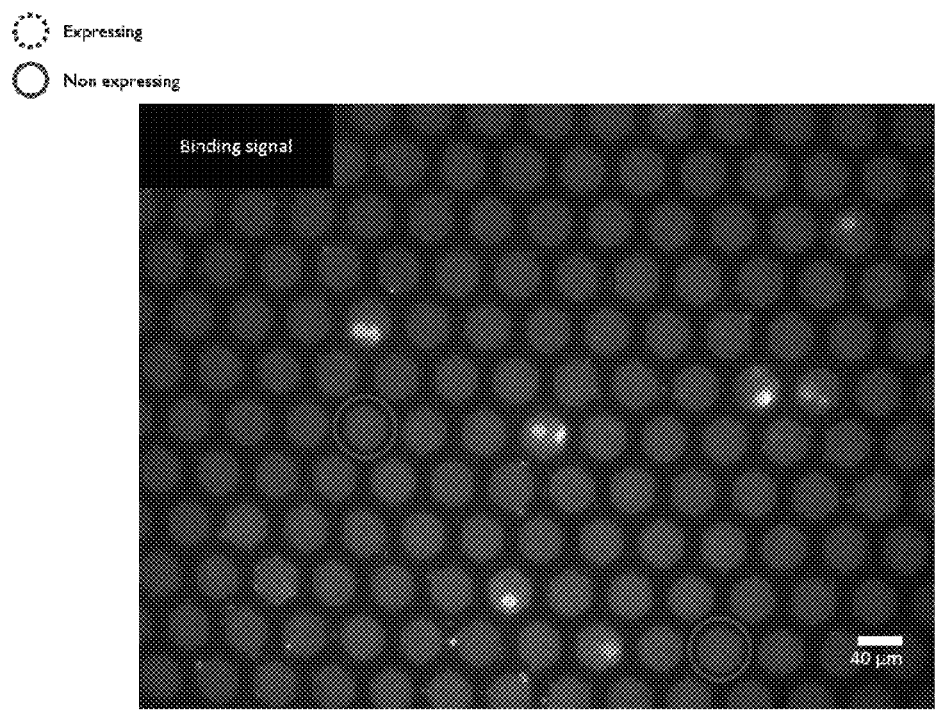

FIGS. 4A and 4B show images of a subsection of the microcapillary array that identifies microcapillaries with expressing and non-expressing cells using bright-field imaging (FIG. 4A) and fluorescence imaging (FIG. 4B).

Example 4. Growth of Cultured Human Cells in a Microcapillary Array

Figure 5A:
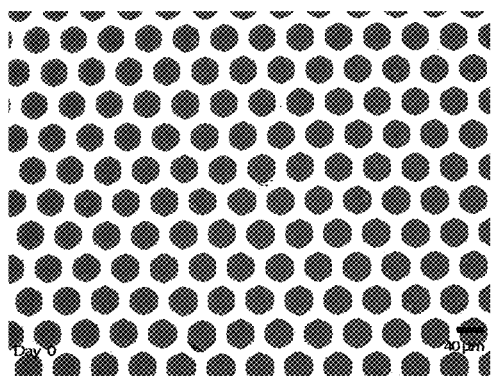
FIGS. 5A-5G illustrate the growth of an immortalized human cell in a microcapillary array over the course of 6 days.
Figure 5B:
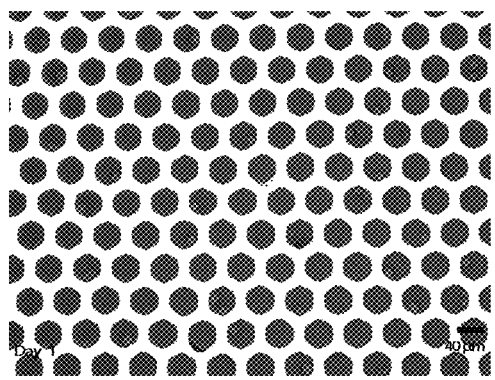
Figure 5C:
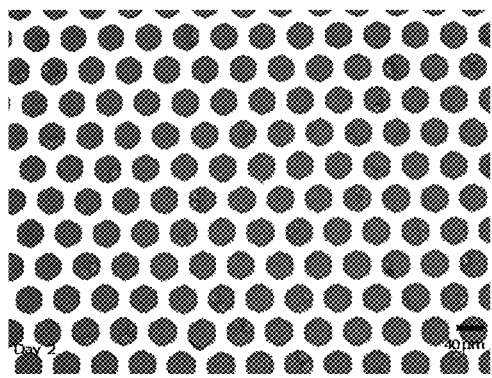
Figure 5D:
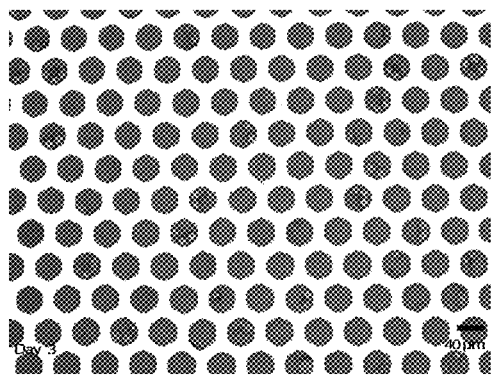
Figure 5E:
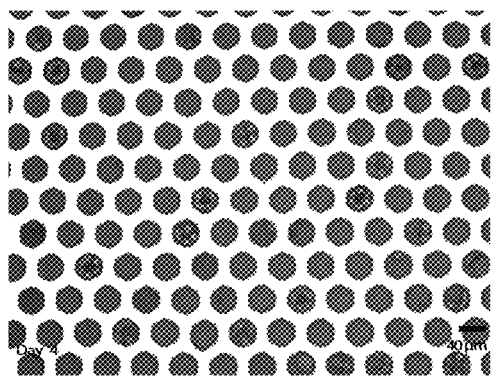
Figure 5F:
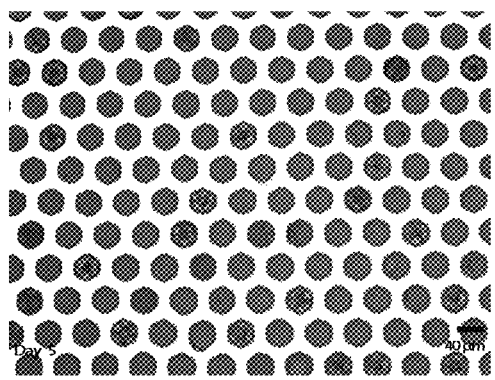
Figure 5G:
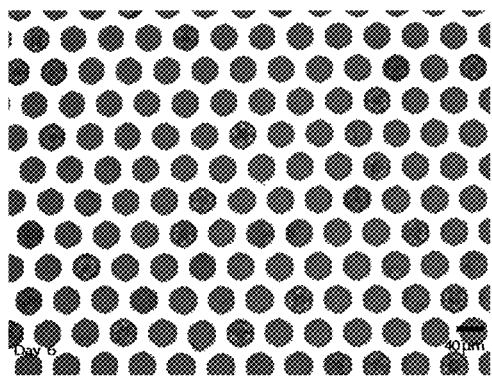

FIGS. 5A-5G demonstrate the growth of K562 cells (a human immortalized myelogenous leukemia cell-line) in growth media over the course of 6 days within an array of microcapillaries. A bright-field image of the same section of the array was taken every 24 hours. FIG. 5A: Day 0; FIG. 5B: Day 1; FIG. 5C: Day 2; FIG. 5D: Day 3; FIG. 5E: Day 4; FIG. 5F: Day 5; and FIG. 5G: Day 6. A 40 μm scale bar is shown in each image.

Example 5. Hybridoma Screening Against Mammalian Reporter Cells

To identify antibody variants that activate specific signaling pathways, hybridomas secreting different antibody variants are added into a microcapillary array with a reporter cell. For example, the reporter cell can be from Qiagen (see http://www.sabiosciences.com/reporter_assay_product/HTML/CCS-013L.html). If a protein variant binds the reporter cell and activates the signaling pathway, the reporter cell expresses a fluorescent protein. The signal fluorescence of activated cells is observed in microcapillaries that contain desirable protein variants and used to isolate the contents of those microcapillaries.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. A method of screening a population of variant proteins comprising the steps of:
    providing a microcapillary array comprising a plurality of microcapillaries, each microcapillary comprising a cellular expression system expressing a variant protein, an immobilized target molecule, and a reporter element, wherein the variant protein associates with the immobilized target molecule in the microcapillary with a particular affinity,
    wherein the cellular expression system is an animal system, a fungal system, a bacterial system, an Insect system, or a plant system; and
    measuring a signal from at least one reporter element that indicates association of at least one variant protein with at least one immobilized target molecule to identify at least one microcapillary of interest wherein the microcapillaries do not contain within them an electromagnetic radiation absorbent material.

2. The method of claim 1, wherein the cellular expression system is a yeast system.

3. The method of claim 1, wherein the target molecule is a target protein or polypeptide, a target nucleic acid, a target carbohydrate, or a combination of each.

4. The method of claim 1, wherein the target molecule is immobilized on a surface.

5. The method of claim 1, wherein the surface is a surface of a cell.

6. The method of claim 4, wherein the target molecule is a native protein.

7. The method of claim 4, wherein the surface is a surface of a bead.

8. The method of claim 1, wherein the reporter element is a labeled antibody or other binding molecule, wherein the labeled antibody or other binding molecule localizes to an epitope on the variant protein.

9. The method of claim 8, wherein the labeled antibody or other binding molecule is a fluorescently-labeled antibody or other binding molecule.

10. The method of claim 8, wherein the labeled antibody is a primary or a secondary antibody.

11. The method of claim 8, wherein the labeled antibody or other binding molecule is an enzyme-linked antibody or other binding molecule.

12. The method of claim 1, wherein the reporter element is activated within a cell, and the target molecule is immobilized on a surface of the cell.

13. The method of claim 12, wherein the reporter element comprises a green fluorescent protein or variant.

14. The method of claim 1, wherein the signal is a fluorescent signal, an absorbance signal, a bright-field signal, or a dark-field signal.

15. The method of claim 1, wherein each microcapillary in the microcapillary array comprises 0 to 5 variant proteins from the population of variant proteins.

16. The method of claim 1, wherein the microcapillary array comprises at least 100,000, at least 300,000, at least 1,000,000, at least 3,000,000, or at least 10,000,000 microcapillaries.

17. The method of claim 1, wherein the microcapillary array comprises at least 100,000, at least 300,000, at least 1,000,000, at least 3,000,000, or at least 10,000,000 microcapillaries.

18. The method of claim 1, wherein the signal is measured by an optical detector.

19. The method of claim 1, wherein the signal is measured by a microscope.

20. The method of claim 1, further comprising the step of isolating the contents of the microcapillary of interest.

21. The method of claim 20, wherein the contents of the microcapillary of interest are isolated by pulsing the microcapillary of interest with a laser.

22. The method of claim 1, wherein the cellular expression system is an animal system.

23. The method of claim 22, wherein the animal system is a mammalian system.

24. The method of claim 1, wherein the cellular expression system is a fungal system.

25. The method of claim 24, wherein the fungal system is a yeast system.

26. The method of claim 1, wherein each microcapillary further comprises an agent to improve viability of the cellular expression system.

27. The method of claim 26, wherein the agent is a growth medium.

28. The method of claim 26, wherein the agent is methylcellulose, dextran pluronic F-68, polyethylene glycol, or polyvinyl alcohol.

* * * * *